(12) United States Patent
Hansen et al.

(10) Patent No.: US 9,445,997 B2
(45) Date of Patent: Sep. 20, 2016

(54) MICROCAPSULES COMPRISING A FAT-SOLUBLE ACTIVE SUBSTANCE

(75) Inventors: Morten Mohr Hansen, Allerød (DK); Nina Musaeus, Hellerup (DK); Carsten Lynggaard Hansen, Smørum (DK)

(73) Assignee: BASF SE (DE)

( * ) Notice: Subject to any disclaimer, the term of this patent is extended or adjusted under 35 U.S.C. 154(b) by 710 days.

(21) Appl. No.: 12/809,664

(22) PCT Filed: Dec. 18, 2008

(86) PCT No.: PCT/EP2008/067887
§ 371 (c)(1),
(2), (4) Date: Sep. 30, 2010

(87) PCT Pub. No.: WO2009/080702
PCT Pub. Date: Jul. 2, 2009

(65) Prior Publication Data
US 2011/0014288 A1    Jan. 20, 2011

(30) Foreign Application Priority Data

Dec. 21, 2007   (EP) ..................................... 07123992

(51) Int. Cl.
| | |
|---|---|
| *A61K 9/16* | (2006.01) |
| *A23D 9/05* | (2006.01) |
| *A23L 1/00* | (2006.01) |
| *A23L 1/30* | (2006.01) |
| *A23L 1/302* | (2006.01) |
| *A23L 1/305* | (2006.01) |
| *A23P 1/04* | (2006.01) |

(52) U.S. Cl.
CPC ............... *A61K 9/1658* (2013.01); *A23D 9/05* (2013.01); *A23K 20/158* (2016.05); *A23K 20/174* (2016.05); *A23K 20/179* (2016.05); *A23K 40/30* (2016.05); *A23L 1/0029* (2013.01); *A23L 1/302* (2013.01); *A23L 1/3006* (2013.01); *A23L 1/3056* (2013.01); *A23P 1/04* (2013.01); *A23V 2002/00* (2013.01)

(58) Field of Classification Search
CPC .. A23L 1/0032; A23L 1/3006; A23L 1/3056; A23P 1/045
USPC ................................. 424/417, 420, 489, 498
See application file for complete search history.

(56) References Cited

FOREIGN PATENT DOCUMENTS

| | | |
|---|---|---|
| EP | 0385081 A2 | 9/1990 |
| EP | 0424578 A1 | 5/1991 |
| JP | S60-49097 A | 3/1985 |
| JP | H02-305898 A | 12/1990 |
| JP | H07-305088 A | 11/1995 |
| WO | WO-91/16292 A1 | 10/1991 |
| WO | WO-94/01001 A1 | 1/1994 |
| WO | WO-01/74175 A1 | 10/2001 |
| WO | WO-03/082313 A1 | 10/2003 |
| WO | WO-2004/009054 A2 | 1/2004 |
| WO | WO-2006/67647 A2 | 6/2006 |
| WO | WO-2008/077401 A1 | 7/2008 |
| WO | WO-2008/077402 A1 | 7/2008 |

OTHER PUBLICATIONS

Baik, M.-Y, et al., "Effects of Antioxidants and Humidity on the Oxidative Stability of Microencapsulated Fish Oil", JAOCS, (2004), vol. 81, No. 4, pp. 355-360.

*Primary Examiner* — Kevin Hill
(74) *Attorney, Agent, or Firm* — Drinker Biddle & Reath LLP

(57) ABSTRACT

The invention relates to microcapsule comprising at least one fat-soluble active substance selected from provitamins, vitamins and esters thereof, monounsaturated fatty acids, polyunsaturated fatty acids (PUFA's), carotenoids and benzoquinones embedded in a matrix comprising a hydrocolloid and optionally one or more other matrix components, wherein the content of active substance(s) is from 30 to 60% of total weight of the microcapsule, and wherein the ratio between said fat-soluble active substance(s) and said hydrocolloid is at least 4:1, as well as a process for preparing such microcapsules.

The microcapsules of the invention may be used for the preparation of tablets, food products and other products including an active substance.

22 Claims, No Drawings

MICROCAPSULES COMPRISING A FAT-SOLUBLE ACTIVE SUBSTANCE

RELATED APPLICATIONS

This application is a national stage application (under 35 U.S.C. §371) of PCT/EP2008/067887, filed Dec. 18, 2008, which claims benefit of European Application No. 07123992.5, filed Dec. 21, 2007.

FIELD OF INVENTION

The present invention relates to microcapsules comprising fat-soluble active substances having a low content of free surface fat, a process for preparing such microcapsules as well as their use and products comprising the microcapsules.

BACKGROUND OF THE INVENTION

Products comprising fat-soluble active substances encapsulated in a hydrocolloid matrix find wide spread use in all kinds of human and animal products, such as food, food supplements, beverages, pharmaceutical, agricultural and veterinary products and personal care products. The purpose is to protect the oxidation sensitive active substance from oxygen and other substances, which attack the substance in order to avoid off-flavour and loss of physiological activity, e.g. during transport, and to increase the shelf life of the products.

When encapsulating fat-soluble active substances an important and acknowledged quality parameter is the content of free surface fat. If the product is not substantially free of free surface fat, e.g. if the content of free surface fat in a product comprising polyunsatutared fatty acids (PUFA's) is more than 1-2%, the quality of the product is significantly impaired and the product will quickly deteriorate through oxidation. PUFA-products complying with this quality parameter normally can not hold more than 25-30% of active substance. Besides, products comprising an increased content of fat-soluble active substance must traditionally be produced by using also an increased amount of hydrocolloid.

Hogan et al in J. Agric. Food Chem. (2001) Vol 49, No. 4, pages 1934-1938, describes microencapsulating properties of sodium caseinate when used in emulsions of soy oils. The effect of increasing the oil/protein ratio on protein load is tested, and it appears that increasing the oil/protein ratio from 0.25 to 3.0 resulted in a progressive decrease in microencapsulation efficiency.

Vega et al in Jour. Dairy Sci. (2006) Vol. 89, No. 2, pages 383-401 describes emulsions with oil-to-protein ratios ranging from 0.25 to 5. Surface fat was reduced from 30% to less than 5%, when lactose was added to an emulsion containing 30% oil.

Vega et al in Int. Dairy Jour. (2007) Vol. 17, No. 6, pages 683-695 describes spray drying of an anhydrous milk fat emulsion stabilized by caseinate or milk protein isolate with trehalose or lactose as encapsulants. The solvent extractable surface free fat values for the spray dried emulsions are determined, and it appears that the higher oil-to-protein ratios, the higher surface free fat.

WO 94/01001 describes microencapsulated oil and fat products, wherein a ratio oil-to-caseinat between about 2.25:1 and 2.75:1 is used. The resulting products hold e.g. 25% fat or oil.

WO 01/74175 describes encapsulated oil products with a rather high content of oil of up to 60%. The resulting products have a high content of free surface fat and/or a relatively high content of hydrocolloid.

The object of the present invention is to provide microcapsules having both a high content of fat-soluble active substance and a desirable low content of free surface fat as well as a new process for preparation thereof.

A further object of the invention is to provide microcapsules with a high content of fat-soluble active substance wherein a corresponding increase in the content of hydrocolloid is avoid.

It is a further object of the invention to provide microcapsules having storage and transportation stability as well as mechanical strength and improved performance during the further processing into tablets, extrudates and the like.

SUMMARY OF THE INVENTION

The present invention relates to a microcapsule comprising at least one fat-soluble active substance selected from provitamins, vitamins and esters thereof, monounsaturated fatty acids, oils comprising polyunsaturated fatty acids (PUFA oils), carotenoids and benzoquinones embedded in a matrix comprising a hydrocolloid and optionally one or more other matrix components, wherein the content of active substance(s) is from 30 to 60% of total weight of the microcapsule, and wherein the ratio between said fat-soluble active substance(s) and said hydrocolloid is at least 4:1.

The invention further relates to a process of preparing a microcapsule, which process comprises the steps of
- providing a solution or dispersion of said hydrocolloid and said optionally other matrix components,
- adding to said solution or dispersion said at least one fat-soluble active substance selected from provitamins, vitamins and esters thereof, monounsaturated fatty acids, oils comprising polyunsaturated fatty acids (PUFA oils), carotenoids and benzoquinones,
- treating the mixture thus obtained to prepare a solution or dispersion of said at least one active substance in said matrix,
- finely dividing and drying the mixture thus obtained to prepare a mass of particles each containing said at least one active substance embedded in said matrix, wherein said at least one active substance and said hydrocolloid are used in a ratio of at least 4:1.

It has surprisingly been found that by using a high oil-to-hydrocolloid ratio in the preparation of the microcapsule, it becomes possible to include a much higher amount of fat-soluble active substance in the final product, and at the same time still maintain a low content of free surface fat. If for instance the product is a PUFA-product, an amount of at least 30%, 40% PUFA or even 60% can be included in the product while simultaneously keeping the content of free surface fat as low as 2% or even 1%. In most cases the content of free surface fat is less than 1%, e.g. less than 0.5% or less than 0.3%, 0.2% or 0.1% of the total weight of the microcapsule.

By the conventional process used until now attempts to include a higher amount than 25-30% fat-soluble active substance often lead to an undesirable substantial increase in free surface fat.

By the process of the invention it has also surprisingly become possible to increase the amount of active substance without increasing the amount of hydrocolloid correspondingly. By the conventional process used attempts to include a higher amount of active substance also required the use of higher amounts of hydrocolloid. Thus, the process used for preparing the microcapsules of the invention is cost-efficient.

When the amount of free surface fat decreases the encapsulation efficiency improves, because less free fat on the surface of the microcapsule is subjected to oxidation. Therefore, the microcapsule becomes more mechanically and chemically stable during storage, transport and further processing into tablets and extrudates or use in food mixes.

The term "microcapsules" as used herein means particles each comprising a matrix material having embedded therein a plurality of solid or liquid micro particles or solute molecules. Microcapsules usually have a mean diameter of about 5 mm or smaller, e.g. between 1 mm and 0.05 mm, such as between 0.6 and 0.1 mm. They can also have a diameter e.g. between 2 mm and 0.01 mm, such as between 1.5 mm and 0.2 mm.

The term "dispersion" as used herein covers both an emulsion meaning a mixture comprising liquid particles (e.g. oil droplets) dispersed in a liquid medium, e.g. water/aqueous solution, or a suspension meaning solid particles dispersed in an liquid medium, e.g. water/aqueous solution.

The terms "free surface fat" or "free fat" as used herein means the fat that is readily extractable by organic solvent under specified conditions. This fat is susceptible to oxidization. The free fat is located on the particle surface, as fat globules just below the particle surface or in contact with capillaries or as dissolution fat almost touching already extracted fat globules. The free surface fat as defined in connection with the invention is determined as described in the example.

DETAILED DESCRIPTION OF THE INVENTION

In one embodiment of the invention the content of active substance(s) is at least 32.5%, such as at least 35%, at least 37.5% or at least 40% of total weight of the microcapsule. It may also be at least 42.5%, at least 45% or at least 47.5% of total weight of the microcapsule.

In other embodiments the ratio between said fat-soluble active substance(s) and said hydrocolloid is at least 5:1, e.g. at least 6:1, at least 7:1 or at least 8:1.

The fat-soluble active substances comprised in the microcapsule of the invention or the microcapsule prepared according to the present invention is a substance which during storage, transport, handling and use requires protection, e.g. from oxygen, moisture, light radiation, and physical influences, in order to avoid physical and chemical decomposition of the substance. These active substances are further defined as being active in either a chemical or biological system.

Active substances suitable for use in connection with the present invention are provitamins and vitamins, e.g. vitamin A and esters thereof, vitamin E and esters thereof, e.g. E-acetate, vitamin D and K, e.g. D2, D3 and K1, monounsaturated fatty acids and polyunsaturated fatty acids (PUFA's), which may be added in the form of fish oil containing i.a. the (n-3) fatty acids docosahexaenoic acid (DHA) and eicosapentaenoic acid (EPA), conjugated linolenic acid (CLA), carotenoids, e.g. β-carotene, lutein, lycopene, β-cryptoxanthin, astaxanthin, cantaxanthin, citranaxanthin and zeaxanthin, curcumin and benzoquinones, e.g. coenzyme Q10 (ubidecarenone).

According to one embodiment the fat soluble active substance is vitamin E or E-acetate, vitamin A, vitamin D2, D3 or K1, a monounsaturated fatty acid or a PUFA (an oil comprising poly unsaturated fatty acids), β-carotene, lycopene, lutein or Q10.

The matrix hydrocolloid of the invention may be any conventional material, such as a protein, e.g. caseinate, whey protein, milk protein or hydrolysates, naturally occurring and modified polysaccharides and naturally occurring hydrocolloids, e.g. alginate, carrageenan, gelatine, gum acacia, modified gum acacia, pectins, modified pectins or mixtures. Starch derived from a natural source, such as potato, wheat, maize, tapioca and rice, and modified starch are other examples of suitable matrix hydrocolloids, e.g. sodium octenyl succinate modified starch.

In one embodiment the hydrocolloid is sodium or potassium caseinate.

In one embodiment of the process of the invention for preparing the microcapsule said fat-soluble active substance(s) and said hydrocolloid is used in a ratio of at least 5:1 or at least 6:1, e.g. at least 7:1 or at least 8:1.

The matrix can optionally comprise further components, such as dissolved carbohydrates, e.g. sorbitol and sucrose, and/or an antioxidant.

The microcapsule may further contain conventional additives such as antioxidants, e.g. t-butylhydroxytoluene (BHT), t-butylhydroxyanisole (BHA), ascorbic acid, ascorbyl palmitate, sodium ascorbate, citric acid, sodium citrate, EDTA or its salts, tocopherols, TBHQ, ethoxyquine, propyl gallate, and extracts from herbs, i.a. rosemary or oregano extract; anti-caking agents, e.g. tri-calcium phosphate and silicates, i.a. silicon dioxide and sodium aluminium silicate; plasticizers, e.g. carbohydrates and carbohydrate alcohols, examples of which are saccharose, glucose, fructose, lactose, invert sugar, sorbitol, mannitol, Trehalose, Tagatose, Pullulan, Raftilose (oligofructose), dextrin, maltodextrin, glycerin, and mixtures thereof, such as saccharose, Trehalose, Pullulan, dextrin and Raftilose and mixtures thereof, emulsifiers and surfactants, e.g. ascorbyl palmitate, sucrose esters, mono- and diglycerides of fatty acids and derivatives thereof, and lecithin.

The dividing and drying of the solution or dispersion to produce a mass of particles can be done in any conventional way, such as spray cooling, spray drying or sheet drying and crushing, see e.g. WO 91/06292.

In one embodiment of the process of the invention a powdering agent, such as corn starch, is fed to the microcapsules during the finely dividing and drying step.

The present invention also relates to a product comprising the microcapsule according to the present invention. According to one embodiment of the invention, this product is a food, a food supplement, a beverage, a pharmaceutical or veterinary product, a feed or feed supplement, a personal care product or a household product.

The products prepared according to the method of the invention are as well suitable for a wide variety of applications, such as the ones described above.

Finally, the invention relates to the use of microcapsules of the invention for the manufacture of tablets or other solid masses containing an active substance.

The process of the invention may be carried out in accordance with the following general recipe or as shown in the examples:

The water soluble ingredients, including the matrix components, are added to hot water and dissolved under agitation. The fat-soluble ingredients are mixed and then added to the aqueous phase and the mixture is treated to prepare a solution or dispersion. The solution or dispersion is diluted, if necessary, to an appropriate viscosity before the solution or dispersion is finely divided and dried by a conventional method.

If applicable a powdering agent is added during the diving and drying.

The free surface fat is determined by extraction from the final microcapsule product by a suitable solvent, such as carbontetrachloride, petroleum ether or n-pentane.

The invention will now be described in further detail with reference to the following examples.

EXAMPLES

Test Method: Determination of Free Surface Fat

Principle:

The microcapsules are dispersed in petroleum ether, whereby the amount of fat which is not encapsulated dissolves and is determined by means of weight analysis. Free fat is expressed as the extracted amount of fat in relation to the weighed amount of product.

Method:

Weigh 10.00 g (±0.50 g) product into a 250 mL Erlenmeyer flask.

Add 50.0 mL petroleum ether to the flask and shake for a few seconds. Decant the petroleum ether into a counterbalanced 100 mL Erlenmeyer flask through a Whatman No. 4 paper filter, which has been moistened with petroleum ether. Repeat the procedure with another 50 mL petroleum ether and again with 2×10 mL petroleum ether.

Evaporate the entire amount of petroleum under nitrogen at max. 40° C. and place the flask in an incubator at 105° C. for one hour and allow to cool in a desiccators.

Weigh the flask in grams (4 decimals).

Calculate the content of free fat (%) in the samples by the following equation:

$$\frac{(m_2 - m_1) * 100}{m_{sample}}$$

$m_1$ = Weight of flask (g)

$m_2$ = Weight of flask with free fat (g)

$m_{sample}$ = Weighted sample (g)

Examples According to the Invention

Example 1

A PUFA Product with PUFA Oil:Caseinate Ratio 8:1

389 g potassium caseinate, 1700 g sucrose and 312 g sodium ascorbate were dissolved in 1200 ml water at 65° C. under agitation. 3117 g PUFA oil (comprising 60 mg/g eicosapentaenoic acid (EPA) and 260 mg/g docosahexaenoic acid (DHA)) was mixed with an antioxidant, heated to 65° C. and added to the aqueous solution and stirred.

The dispersion was homogenised in a rotor/stator system; alternatively a high pressure homogeniser can be applied; and diluted to a sprayable viscosity.

Subsequently the dispersion was atomised in a spray drying tower, where the dispersion particles were covered with a thin layer of starch and dried.

The resulting dry powder had the following characteristics:
Content of PUFA oil: 42.0%,
Free Fat: 0.2%

Example 2

A PUFA Product with PUFA Oil:Caseinate Ratio 10:1

332 g potassium caseinate, 1356 g sucrose and 252 g sodium ascorbate were dissolved in 1100 ml water at 65° C. under agitation. 3324 g PUFA oil (comprising 60 mg/g eicosapentaenoic acid (EPA) and 260 mg/g docosahexaenoic acid (DHA)) was mixed with an antioxidant, heated to 65° C. and added to the aqueous solution and stirred.

The dispersion was homogenised in a rotor/stator; alternatively a high pressure homogeniser can be applied; and diluted to a sprayable viscosity.

Subsequently the dispersion was atomised in a spray drying tower, where the dispersion particles were covered with a thin layer of starch and dried.

The resulting dry powder had the following characteristics:
Content of PUFA oil: 45.9%,
Free Fat: 0.27%

Dispersions and microcapsules with other ratios of fat-soluble active substance/hydrocolloid were prepared in a similar way. The results are given in Table 1.

Example 3

PUFA products with other ratios of PUFA oil:caseinate were prepared in a similar way. The results are given in the Table.

TABLE

| Target % oil | PUFA oil:caseinate Ratio w:w | Total fat in final dry product % | Free fat in final dry product % |
|---|---|---|---|
| 35% | 6:1 | 36.0 | 0.16 |
| 40% | 4:1 | 43.0 | 1.81 |
| 40% | 5:1 | 42.9 | 1.08 |
| 40% | 6:1 | 43.8 | 0.76 |
| 40% | 8:1 | 42.0 | 0.22 |
| 45% | 8:1 | 48.1 | 1.03 |
| 45% | 10:1 | 47.3 | 0.71 |

Comparative Examples

Comparative Example 1

A PUFA Product with PUFA Oil:Caseinate Ratio 2:1

3000 g potassium caseinate, 6000 g sucrose and 1356 g sodium ascorbate were dissolved in 1400 ml water at 65° C. under agitation. 6002 g PUFA oil (comprising 60 mg/g eicosapentaenoic acid (EPA) and 260 mg/g docosahexaenoic acid (DHA)) was mixed with an antioxidant, heated to 65° C. and added to the aqueous solution and stirred.

The dispersion was homogenised well in a rotor/stator; alternatively a high pressure homogeniser can be applied; and diluted to a sprayable viscosity.

Subsequently the dispersion was atomised in a spray drying tower, where the dispersion particles were covered with a thin layer of starch and dried.

The resulting dry powder had the following characteristics:
Content of PUFA: 26.8%,
Free Fat: 0.04%

Comparative Example 2

A PUFA Product with PUFA Oil:Caseinate Ratio 3:1

487 g potassium caseinate, 492 g sucrose and 146 g sodium ascorbate were dissolved in 1400 ml water at 65° C. under agitation. 1460 g PUFA oil (comprising 60 mg/g eicosapentaenoic acid (EPA) and 260 mg/g docosahexaenoic acid (DHA)) was mixed with an antioxidant, heated to 65° C. and added to the aqueous solution and stirred.

The dispersion was homogenised well in a rotor/stator system; alternatively a high pressure homogeniser can be applied; and diluted to a sprayable viscosity.

Subsequently the dispersion was atomised in a spray drying tower, where the dispersion particles were covered with a thin layer of starch and dried.

The resulting dry powder had the following characteristics:
Content of PUFA: 45.9%,
Free Fat: 2.68%

Comparative Example 3

A PUFA product with PUFA oil:caseinate ratio of 3.5:1 was prepared in a similar way. The resulting dry powder had the following characteristics:
Content of PUFA: 49.4%,
Free Fat: 13.6%

The invention claimed is:

1. A microcapsule comprising at least one fat-soluble active substance selected from provitamins, vitamins and esters thereof, monounsaturated fatty acids, oils comprising polyunsaturated fatty acids (PUMA oils), carotenoids and benzoquinones embedded in a matrix comprising a hydrocolloid and optionally one or more other matrix components, wherein the content of active substance(s) is from 30 to 40% of total weight of the microcapsule, and the ratio between said fat-soluble active substance(s) and said hydrocolloid is at least 5:1.

2. The microcapsule of claim 1, wherein the active substance is vitamin E or E-acetate, vitamin A, D2, D3 or K1, a monounsaturated fatty acid or a PUPA oil, β-carotene, lycopene, lutein or Q10.

3. The microcapsule of claim 1, wherein the content of active substance(s) is at least 35% of total weight of the microcapsule.

4. The microcapsule of claim 1, wherein the ratio between said fat-soluble active substance(s) and said hydrocolloid is from 5:1 to 10:1.

5. The microcapsule of claim 1, wherein the hydrocolloid is a protein.

6. The microcapsule of claim 5, where in the hydrocolloid is a caseinate, e.g. sodium or potassium caseinate.

7. The microcapsule of claim 1, wherein the matrix further contains antioxidants and/or carbohydrates.

8. A product comprising the microcapsule of claim 1.

9. The product of claim 8, wherein the content of free surface fat in the microcapsule is less than 2% by weight based on the microcapsule.

10. The product of claim 9, wherein the content of free surface fat in the microcapsule is less than 1% by weight based on the microcapsule.

11. The microcapsule of claim 1, wherein the content of free surface fat in the microcapsule is less than 2% by weight based on the microcapsule.

12. The microcapsule of claim 11, wherein the content of free surface fat in the microcapsule is less than 1% by weight based on the microcapsule.

13. The microcapsule of claim 1, wherein the matrix further comprises at least one antioxidant.

14. A microcapsule comprising at least one fat-soluble active substance selected from provitamins, vitamins and esters thereof, monounsaturated fatty acids, oils comprising polyunsaturated fatty acids (PUFA oils), carotenoids and benzoquinones embedded in a matrix comprising a hydrocolloid and optionally one or more other matrix components, wherein the content of active substance(s) is from 30 to 45% of total weight of the microcapsule, and wherein the ratio between said fat-soluble active substance(s) and said hydrocolloid is at least 6:1.

15. The microcapsule of claim 14, wherein the content of active substance(s) is at least 40% of total weight of the microcapsule.

16. The microcapsule of claim 14, wherein the ratio between said fat-soluble active substance(s) and said hydrocolloid is from 6:1 to 8:1.

17. The microcapsule of claim 16, wherein the content of free surface fat in the microcapsule is less than 1% by weight based on the microcapsule.

18. A microcapsule comprising at least one fat-soluble active substance selected from provitamins, vitamins and esters thereof, monounsaturated fatty acids, oils comprising polyunsaturated fatty acids (PUFA oils), carotenoids and benzoquinones embedded in a matrix comprising a hydrocolloid and optionally one or more other matrix components, wherein the content of active substance(s) is from 30 to 48% of total weight of the microcapsule, and wherein the ratio between said fat-soluble active substance(s) and said hydrocolloid is at least 8:1.

19. A microcapsule comprising at least one fat-soluble active substance selected from provitamins, vitamins and esters thereof, monounsaturated fatty acids, oils comprising polyunsaturated fatty acids (PUFA oils), carotenoids and benzoquinones embedded in a matrix comprising a hydrocolloid and optionally one or more other matrix components, wherein the content of active substance(s) is from 30 to 60% of total weight of the microcapsule, and wherein the ratio between said fat-soluble active substance(s) and said hydrocolloid is at least 10:1.

20. A process of preparing the microcapsule of claim 1, which process comprises the steps of
providing a solution or dispersion of said hydrocolloid and said optionally other matrix components,
adding to said solution or dispersion said at least one fat-soluble active substance selected from provitamins, vitamins and esters thereof, monounsaturated fatty acids, oils comprising polyunsaturated fatty acids (PUFA oils), carotenoids and benzoquinones,
treating the mixture thus obtained to prepare a solution or dispersion of said at least one active substance in said matrix,
finely dividing and drying the mixture thus obtained to prepare a mass of particles each containing said at least one active substance embedded in said matrix,
wherein said at least one active substance and said hydrocolloid are used in a ratio of at least 5:1, when the content of active substance(s) is from 30 to 40% of the total weight of the microcapsule.

21. The process of claim 20, wherein said at least one active substance and said hydrocolloid are used in a ratio of at least 6:1.

22. The process of claim 21, wherein said at least one active substance and said hydrocolloid are used in a ratio of at least 8:1.

* * * * *